United States Patent
Von Oppen Bezalel et al.

(10) Patent No.: US 8,398,958 B2
(45) Date of Patent: Mar. 19, 2013

(54) CAROTENOID COMPOSITIONS USEFUL FOR WHITENING SKIN

(75) Inventors: Liki Von Oppen Bezalel, Berlin (DE); Etienne Soudant, Paris (FR); Inon Perry, Tel-Aviv (IL); Fumio Maniwa, Tokyo (JP); Yuki Hata, Tokyo (JP); Akemi Takayama, Tokyo (JP)

(73) Assignee: I.B.R. Israeli Biotechnology Research Ltd., Ramat Gan (IL)

( * ) Notice: Subject to any disclaimer, the term of this patent is extended or adjusted under 35 U.S.C. 154(b) by 663 days.

(21) Appl. No.: 12/306,888

(22) PCT Filed: May 29, 2007

(86) PCT No.: PCT/IL2007/000648
§ 371 (c)(1), (2), (4) Date: Jul. 14, 2009

(87) PCT Pub. No.: WO2008/004206
PCT Pub. Date: Jan. 10, 2008

(65) Prior Publication Data
US 2009/0311204 A1    Dec. 17, 2009

(30) Foreign Application Priority Data
Jul. 2, 2006 (IL) .......................... 176668

(51) Int. Cl.
A61K 8/31 (2006.01)
A61K 7/42 (2006.01)
A61K 7/00 (2006.01)
A61K 31/04 (2006.01)
A61Q 17/04 (2006.01)
A61Q 19/02 (2006.01)
A23L 1/30 (2006.01)

(52) U.S. Cl. .............. 424/59; 424/62; 424/401; 426/73; 426/542; 514/725

(58) Field of Classification Search .................... 424/59, 424/62, 401; 426/73, 542; 514/725
See application file for complete search history.

(56) References Cited

U.S. PATENT DOCUMENTS

| | | | |
|---|---|---|---|
| 5,747,006 | A | 5/1998 | Dornoff |
| 5,980,904 | A | 11/1999 | Leverett |
| 6,110,478 | A | 8/2000 | Harang |
| 6,342,254 | B1 | 1/2002 | Soudant |

(Continued)

FOREIGN PATENT DOCUMENTS

| EP | 0467795 B2 | 1/1992 |
|---|---|---|
| EP | 1 175 898 | 1/2002 |

(Continued)

OTHER PUBLICATIONS

International Search Report for PCT/IL2007/000648 dated Feb. 28, 2008 (6 sheets).

(Continued)

*Primary Examiner* — Ernst Arnold
*Assistant Examiner* — Hong Yu
(74) *Attorney, Agent, or Firm* — Rodney J. Fuller; Booth Udall Fuller, PLC

(57) ABSTRACT

The present invention relates to use of carotenoid preparations for promoting skin whitening. Particularly, the present invention discloses that a combination of phytoene and phytofluene is effective in whitening skin. The present invention further relates to carotenoid compositions comprising a combination of phytoene and phytofluene effective in whitening skin and at least one additional carotenoid, particularly carotenoids devoid of highly intense color.

15 Claims, 2 Drawing Sheets

U.S. PATENT DOCUMENTS

| | | |
|---|---|---|
| 6,383,474 B1 | 5/2002 | Soudant |
| 6,994,874 B2 | 2/2006 | Leverett |
| 7,029,709 B2 | 4/2006 | Arquette |
| 2004/0010826 A1 | 1/2004 | Hauptmann et al. .......... 800/323 |

FOREIGN PATENT DOCUMENTS

| | | |
|---|---|---|
| JP | 6279257 B2 | 10/1994 |
| JP | 2003-532680 A | 8/2002 |
| JP | 2002-524403 A | 11/2003 |
| JP | 2004300117 A1 | 10/2004 |
| WO | WO/00/13654 | 3/2000 |
| WO | WO/02/58683 | 1/2002 |
| WO | WO/03/041678 | 5/2003 |

OTHER PUBLICATIONS

Written Opinion of the International Searching Authority for PCT/IL2007/000648 dated Feb. 28, 2008 (8 sheets).

Aust, Olivier et al., "Supplementation with tomato-based products increases lycopene, phytofluene, and phytoene levels in human serum and protects against UV-light-induced erythema", Int J Vitam Nutr Res., 75(1):54-60 (2005).

Hata, Tissa R. et al., "Non-Invasive Raman Spectroscopic Detection of Carotenoids in Human Skin", J. Invest. Dermatology, 115(3):441-448 (2000).

Fragrance Journal, vol. 32, p. 107-108; Sep. 2004.

von Oppen-Bezalel et al., "IBR-CLC, Colorless Carotenoids: Phytoene and Phytofluene from Unicellular Algae—Applications in Cosmetics, Wellness and Nutrition", Fragrance Journal, 34:48-53, (Mar. 15, 2006).

Aust et al., "Supplementation with tomato-based products increases lycopene, phytofluene, and phytoene levels in human serum and protects against UV-light-induced erythema", Int J Vitam Nutr Res., 75(1):54-60 (Jan. 2005).

Counterpart Japanese Patent Application No. 2007-030836 Office Action dated Mar. 2, 2012, English translation.

CAROTENOID COMPOSITIONS USEFUL FOR WHITENING SKIN

RELATED APPLICATION DATA

This application is the U.S. national stage of PCT/IL2007/000648 filed on May 29, 2007, which is based on and claims the benefit of Israeli Patent Application No. 176668 filed on Jul 2, 2006, the content of each of which is expressly incorporated herein in its entirety by reference hereto.

FIELD OF THE INVENTION

The present invention relates to methods for promoting skin whitening utilizing compositions comprising the carotenoids phytoene and phytofluene and optionally additional carotenoids, particularly carotenoids devoid of highly intense color.

BACKGROUND OF THE INVENTION

Skin color is primarily determined by the amount of the pigment melanin present in melanocytes, cells that are present in the epidermal basal layer of the skin. Melanin production takes place in unique organelles within the melanocytes, known as melanosomes, and protects the skin from the harmful effects of UV light. Darker skin tone of certain societies results from a naturally increased production of melanin, and high production in response to the stimulus of UV light leads to the well-known tanning effect of the skin. Aging, exposure to sun, hormonal abnormalities and various skin disorders increase the deposition of melanin pigment in skin, resulting in dark spots and freckles. Such dark spots are not only considered to be unattractive in many societies, they are also known to be unhealthy and therefore undesired.

For those who are interested in eliminating the presence of dark spots on the skin or a lighter skin tone, whitening or bleaching compositions are useful. Many modern skin-bleaching compositions either destroy melanin (typically by destroying or disrupting melanin granules), inhibit its formation (often by inhibiting tyrosinase, a melanin biosynthetic enzyme, or by inhibiting melanocyte activity and proliferation), or both. Many of these bleaching compositions contain harsh chemicals such as peroxides, acids or formaldehyde, or thiolated materials such as glutathione, cysteine, mercaptosuccinic acid, mercaptodextran, and mercaptoethanol. These chemicals, in addition to having stringent effects on skin, have an objectionable odor that makes products containing them undesirable to a consumer.

Less stringent therapies have other disadvantages. For example, hydroquinone is used as a whitening agent as it acts by suppressing melanocyte activity. However, hydroquinone is oxidized by air, light, and tyrosinase itself. The oxidized products of hydroquinone have been implicated in skin irritation and inflammation (and perhaps cytotoxicity) and in pigmentation rebound (i.e. initial lightening followed by darkening). In addition, due to these oxidation processes, the shelf life of preparations containing hydroquinone and its bioavailability upon application are relatively short.

Typical whitening agents in cosmetic formulations are kojic acid, arbutin, licorice extract and vitamin C. These are effective tyrosinase inhibitors and anti oxidants, but are usually not stable as they are easily oxidized and degraded.

European Patent No. EP0467795 discloses the use of paucilamellar liposomal carriers for transporting active molecules across the cell membrane, including molecules which induce reduction of melanosome formation by diversion of the enzymatic activity, resulting in hyperactivation of the melanin-degrading enzymes. That patent also discloses dermatological or cosmetic compositions based on these carriers and to their uses in the elimination or attenuation of dyschromia as well as in the treatment of melanoma caused by exposure to sunlight.

Recently, it has been suggested to use naturally derived materials, which are more pleasant to use, some of which have been known in ancient therapies to have whitening effects. These include the use of lemon, orange, cucumber, ginko, carob, rose fruit, geranium herb, cinnamon, sweet marjoram, rosemary, clove, mulberry, licorice, bearberry, and acerola cherry extracts, alone or in combination with other whitening agents (for example, see U.S. Pat. Nos. 5,747,006; 5,980,904; 6,994,874; and 7,029,709 among others). The variability of active ingredients in these natural products sometimes limits their usefulness, particularly as skin type, color, age, and condition vary greatly in different subjects, and make suggested dosages and regimens difficult to fashion.

Cosmetic compositions containing carotenoids having a whitening effect have been also disclosed. Japanese Patent No. JP2004300117 discloses a cosmetic composition containing carotenoids and an extract of a plant of the genus *Malus*, preferably the extract of the fruit or fruit juice, wherein the extract preferably contains polyphenols and the carotenoids preferably contain lycopene.

Japanese Patent No. 6279257 discloses a carotenoid or a chloroform extract of *Jatropha podagrica*, belonging to the family Euphorbiaceae, having an inhibitory activity on melanin biosynthesis and cosmetic compositions comprising same for beautifying and whitening skin.

However, carotenoid containing compositions are typically highly colored due to the orange-red color of beta-carotene and lycopene. Beta-carotene and lycopene are sensitive to light and oxidation, a property which considerably limits their use and shortens shelf-life of products containing them (in: Carotenoids, Chemistry and Biology, Krinski, N. I., Matthews-Roth, M. M., Taylor, R. F., eds., Plenum Press, New York, London, 1989). In addition, beta-carotene and lycopene have a distinctive orange color and this color has a serious limitation for use in effective concentrations in a variety of cosmetic or nutraceutical applications. Moreover, composition comprising colored carotenoid like lycopene, beta-carotene, cantaxanthin and the like are known to color the skin when applied topically and moreover, when taken orally, as disclosed, for example, in U.S. Pat. No. 6,110,478. Such compositions are used to achieve skin tanning effects, and commercial products for this purpose are available in the market.

Thus, there is a recognized need for, and it would be highly beneficial to have alternative, effective carotenoid preparations having minimal adverse side effects, which are effective for whitening skin and which are suitable for the cosmetic industry in topical as well as in oral forms.

SUMMARY OF THE INVENTION

The present invention provides methods for skin whitening, as well as compositions comprising carotenoids for skin whitening and related cosmetic applications. Particularly, the compositions of the present invention comprise a combination of the carotenoids phytoene and phytofluene effective in skin whitening, and one or more additional carotenoids, excluding intensely colored carotenoids at concentrations higher than the concentration of the combined total amount of phytoene and phytofluene.

The methods and compositions of the present invention are useful for lightening of skin color, evening or harmonization of skin tone and/or color, reduction of pigmentation, reduction of pigmentation after UV exposure, reduction in the appearance of solar lentigines (age spots) or ephilides (freckles), reduction of melasma, reduction of chloasma, reduction of post-inflammatory hyperpigmentation and reduction of pigmented keratoses.

The present invention is based in part on the unexpected finding that the carotenoids phytoene and phytofluene are effective in controlling melanin production. Some of the inventors of the present invention have previously shown that phytoene and phytofluene possess anti-oxidative properties and are capable of absorbing ultra violet (UV) light, thus are effective, inter alia, in preventing skin damages caused by exposure to UV light and oxidative processes. The present invention now discloses that surprisingly, combinations of phytoene and phytofluene have a direct effect on skin pigmentation by reducing the melanin content in the skin cells.

The teachings of the present invention are advantageous over previously known compositions and methods for skin whitening, as phytoene and phytofluene are natural carotenoids known not to have any adverse effects either when applied to skin or when taken orally, while being highly effective. The combination of phytoene and phytofluene has now been shown to have at least equivalent inhibitory activity on melanogenesis of B16 melanoma cells compared to known skin whitening ingredients such as arbutin.

Unexpectedly, not only does applying the carotenoid compositions of the present invention, either topically or orally, not result in acquiring yellow to orange color by the skin, as often happen upon application of intensely colored carotenoid compositions, the present invention now discloses that these composition are effective in whitening the skin. Without wishing to be bound to any specific mechanism or theory, the whitening effect of the compositions of the present invention is due to reduced content of melanin in the skin, being the result of phytoene and phytofluene activity either on reduction of melanin synthesis, enhancement of melanin degradation or reduction in the proliferative rate of melanocytes in the skin.

Thus, according to one aspect, the present invention provides a method for promoting skin whitening comprising administering to a subject in need thereof a composition comprising a combination of phytoene and phytofluene in an amount effective in whitening skin.

Phytoene and phytofluene from any available source can be used according to the method of the present invention, including phytoene and phytofluene extracted from a natural source, prepared by chemical synthesis or recovered from genetically modified sources.

According to certain embodiments, the method of the present invention employs compositions comprising at least one additional carotenoid other than phytoene and phytofluene. According to one embodiment, the additional carotenoid is selected from the group consisting of zeta-carotene, beta-carotene, lycopene, zeaxanthin, astaxanthin, cataxanthin, zeaxanthin, lutein, canthaxanthin and the like, and any combination thereof. According to further embodiments, the ratio of the combination of phytoene and phytofluene to the other carotenoid is from about 1:1 to about 50:1, alternatively from about 2:1 to about 25:1, still alternatively from about 4:1 to about 10:1. According to one embodiment, the carotenoid other than phytoene and phytofluene is zeta-carotene.

According to certain embodiments, the compositions used with the method of the present invention are devoid of intense color. According to other embodiments, the compositions are essentially colorless.

According to further embodiments, the composition further comprises at least one active ingredient selected from the group consisting of, but not limited to, an anti-oxidant, an anti-inflammatory agent, a moisturizer, a vitamin, a UV absorbing agent a UV protecting agent, IBR-Dormin® (a *Narcissus tazetta* bulb extract, U.S. Pat. No. 6,342,254), skin whitening agent or any combination thereof.

According to certain embodiments, the active ingredient other than phytoene and phytofluene is selected from the group consisting of, omega oils, IBR-Dormin® and vitamin C.

The whitening effect of the combination of phytoene, phytofluene and optionally zeta-carotene can be achieved when a composition comprising same is topically applied to the skin, as well as when the composition is administered orally.

The administration regime and the mode of application of the whitening compositions according to the methods of the present invention will depend on parameters associated with the phenomena to be treated as well as on characteristics of the treated individual (age, size, gender, etc.). According to certain embodiments, the method of the present invention comprises topical application to the skin at a regime selected from at least once a week up to at least twice a day. According to other embodiments, the methods of the present invention comprise oral administration of the whitening carotenoid composition at a regime selected from at least once a week up to at least twice a day. According to other embodiments, an oral composition and a topical composition are administered to the subject concomitantly.

According to another aspect, the present invention provides a composition comprising a combination of phytoene and phytofluene in an amount effective in whitening skin and at least one additional carotenoid, wherein the concentration of the additional carotenoid is at most equal to the concentration of the combined total amount of phytoene and phytofluene. According to certain embodiments, the ratio of the combination of phytoene and phytofluene to the additional carotenoid is from about 1:1 to about 50:1, alternatively from about 2:1 to about 25:1, still alternatively from about 4:1 to about 10:1. Carotenoids other than phytoene and phytofluene which may be present in the compositions are selected from the group consisting of zeta-carotene, beta-carotene, lycopene, zeaxanthin, astaxanthin, cataxanthin, zeaxanthin, lutein, canthaxanthin and the like and any combination thereof.

According to certain embodiments, the composition comprises zeta-carotene in addition to phytoene and phytofluene.

The carotenoids in the compositions of the present invention, particularly phytoene, phytofluene and zeta-carotene, can be obtained from any available source, including, but not limited to, preparation from a natural source, preparation by a chemical synthesis and recovered from genetically modified sources.

According to certain embodiments, each of the carotenoids phytoene, phytofluene and the additional carotenoid, particularly zeta-carotene, is derived from a natural source. According to one embodiment, the carotenoids are derived from the same natural source.

According to one embodiment, phytoene, phytofluene and zeta-carotene are derived from tomato fruit. According to one embodiment, the phytoene, the phytofluene, the zeta-carotene or combinations thereof are present within an oil-soluble tomato extract. According to another embodiment, each of these carotenoids or a combination thereof is present in dry material of tomato fruit. According to certain embodiments, the oil-soluble tomato extract or the dry material of the tomato fruit is essentially devoid of lycopene and beta-carotene.

According to another embodiment, the composition of the present invention comprises phytoene, phytofluene and optionally zeta-carotene derived from an alga. According to one embodiment, the alga is of the *Dunaliella* species. According to one embodiment, the phytoene, the phytofluene, the zeta-carotene or any combination thereof is present within an oil-soluble *Dunaliella* extract. According to another embodiment, each of these carotenoids or a combination thereof is present in *Dunaliella* dry material. According to certain embodiments, the oil-soluble *Dunaliella* extract or the *Dunaliella* dry material is essentially devoid of beta-carotene.

According to yet other embodiments, each of the carotenoids phytoene, phytofluene, and zeta-carotene present within the composition of the present invention is derived from a microorganism.

The carotenoid compositions of the present invention can be in any form as is known in the art, including a solution, a suspension, a dehydrated powder, capsules, tablets, creams, ointments and the like. According to certain embodiments, the compositions of the present invention are in a form of non-aqueous solutions. According to other embodiments, the compositions are in the form of dehydrated powder.

According to certain embodiments, the composition of the present invention is a cosmetic composition. formulated for topical administration. Optionally, the composition further comprises a cosmetically acceptable diluent or carrier. According to certain embodiments, the composition comprises a diluent selected from the group consisting of, but not limited to, squalane, polydecene, squalene, jojoba oil, sunflower oil, and the like. According to one embodiment, the diluent is squalane, typically a naturally derived squalane.

According to certain other embodiments, the cosmetic composition further comprises at least one agent selected from the group consisting of a preservative, a thickener, a dispersing agent, a surfactant, an emulsifier, a buffer, a chelating agent, a colorant, a perfume or any combination thereof.

According to other embodiments, the composition further comprises at least one active ingredient selected from the group consisting of an anti-oxidant, an anti-inflammatory agent, a moisturizer, a vitamin, a UV absorbing agent, a UV protecting agent or any combination thereof.

According to additional certain embodiments, the composition of the present invention is formulated for oral administration.

According to one embodiment, the composition further comprises an excipient, diluent or carrier suitable for oral consumption. According to another embodiment, the composition is formulated in a form selected from the group consisting of a capsule, dragee, pill, tablet, gel, liquid, slurry, suspension and syrup.

Other objects, features and advantages of the present invention will become clear from the following description and drawings.

DETAILED DESCRIPTION OF THE INVENTION

Figure 1:
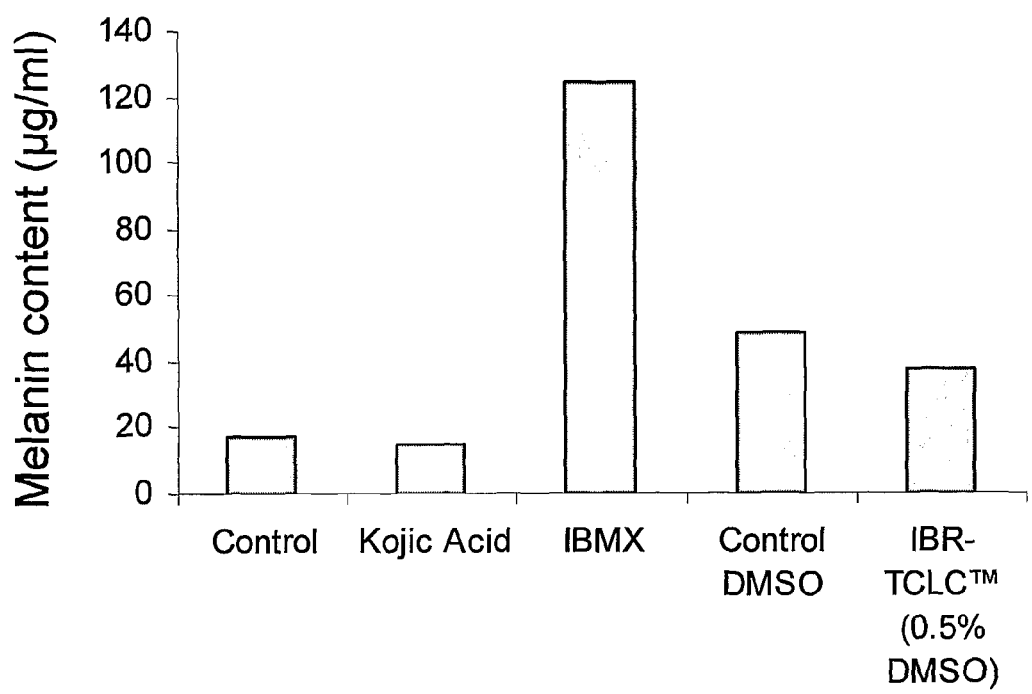
FIG. 1 shows the effect of the compound IBR-TCLC® and reference compounds on melanin synthesis by B16 murine melanoma cells.

The present invention discloses for the first time that a combination of the carotenoids phytoene and phytofluene is highly effective in whitening skin without having any adverse effects on the skin. Thus, the present invention provides a method for whitening skin utilizing such phytoene and phytofluene combination. The present invention also provides carotenoid compositions comprising phytoene, phytofluene and at least one additional carotenoid useful for cosmetic applications. The combination of phytoene and phytofluene is the principle component of the compositions of the present invention, such that the concentration of the additional carotenoid is at most equal to the concentration of the phytoene and phytofluene combination.

Definitions

As used herein, the term "phytoene" refers to 7,7',8,8',11,11',12,12'-octahydro-psi-psi-carotene The term "phytofluene" refers to 15Z,7,8,11,12,7',8'-hexahydro-psi-psi-carotene.

The term "zeta-carotene" refers to 7,8,7',8'-tetrahydro-psi-psi-carotene. Phytoene, phytofluene and zeta-carotene are carotenoids (C-40 isoprenoid chain) which are precursors in the biosynthetic pathway leading to the production of beta-carotene, lycopene and other carotenoids (phytoene is the first carotenoid-specific precursor and phytofluene and zeta-carotene are produced therefrom in a subsequent desaturation steps). Phytoene is completely colorless whereas phytofluene has a slight yellowish color. Zeta-carotene is the first visible carotenoid.

The term "whitening effect" as is used herein means the effect of relieving or eliminating or preventing dark skin, melasma, chloasma, solar lentigines, ephelis and the like generated due to a variety of causative factors including, but not limited to, exposure to ultraviolet rays, change in the hormone balance and genetic programs. In general, and without wishing to be bound to a specific mechanism or theory, it has been found that melanocytes are stimulated by, for instance, exposure to ultraviolet rays and any change in the hormone balance. The melanin pigment biosynthesized in the melanocytes is deposited in the skin and thus cause the skin darkening phenomena described above.

As used herein, the term "amount effective in whitening skin" refers to an amount of phytoene and an amount of phytofluene which, when administered in combination, achieves the desired whitening effect.

As used herein, the term "mass %" refers to a concentration based on weight/weight percentage.

According to one aspect, the present invention provides a method for promoting skin whitening comprising administering to a subject in need thereof a composition comprising a combination of phytoene and phytofluene in an amount effective in whitening skin.

Having fine skin is highly desired by people all over the word, and white skin is considered as preferable in certain populations, particularly at the Far East. Generally, human skin color is determined hereditarily according to the concentration and distribution of melanin in the skin, but it can also be influenced by environmental or physiological conditions such as solar ultraviolet rays, hormonal changes, fatigue and stress. Melanin is produced in melanocytes through a non-enzymatic oxidation reaction after the enzyme tyrosinase acts on the amino acid tyrosine changing it into dopa and dopaquinone. Undesired skin pigmentation is generally due to the activation of melanocytes by the UV rays in sunlight and/or abnormal hormone balance.

Surprisingly, the present invention now shows that a combination of phytoene and phytofluene is highly effective in skin whitening.

As exemplified herein below, the combination of phytoene and phytofluene is highly active in reducing melanin content within melanocytes, having at least equivalent effect to that of kojic acid, a compound known to have inhibiting activity on melanin synthesis. Moreover, the compositions comprising phytoene and phytofluene examined according to the teaching of the present invention have been shown to have no cytotoxic activity; thus, they may be applied to skin in an amount greater than those of existing whitening compounds such as arbutin, which are known to have adverse side effects when applied above certain level. As a result, the overall whitening activity of the compositions of the present invention is expected to be significantly advantageous over hitherto known whitening agents.

It is to be understood that according to the teaching of the present invention any composition comprising a combination of phytoene and phytofluene may be used, providing the amount of the combination is effective in whitening skin, and the composition does not have any adverse effect on the skin, particularly on skin color.

Some of the inventors of the present invention and co-workers have previously disclosed a colorless composition comprising phytoene and phytofluene (International Patent Application Publication No. WO 00/13654). The composition disclosed therein as well as other compositions defined hereinabove and known in the art can be used for whitening skin according to the method of the present invention.

According to another aspect, the present invention provides a composition comprising a combination of phytoene and phytofluene in an amount effective in whitening skin and at least one additional carotenoid, wherein the concentration of the additional carotenoid is at most equal to the concentration of the combined total amount of phytoene and phytofluene.

The phytoene and phytofluene in the composition of the invention may each be either in their trans or in their cis forms.

The weight ratio between the phytoene and phytofluene in the composition of the invention can range between 200:1 to 1:200, respectively, typically between about 50:1 to 1:50, preferably from 10:1 to 1:10, 10:1 (phytoene:phytofluene) being a particular example. The above ratios of phytoene to phytofluene may be reached by using a preparation utilizing an organism having the desired phytoene to phytofluene ratio, using an extract which contains both carotenoids in the desired ratio, by adding an additional amount of one of the carotenoids to an extract comprising both carotenoids so that the desired ratio is obtained, or by mixing the two separate carotenoids (each obtained by any of the methods described herein or are known in the art) to reach the desired ratio between them.

Carotenoids other than phytoene and phytofluene which may be present in the compositions are selected from the group consisting of zeta-carotene, beta-carotene, lycopene, zeaxanthin, astaxanthin, cataxanthin, zeaxanthin, lutein, canthaxanthin and alike and any combination thereof.

According to certain embodiments, the composition of the present invention is devoid of an intense color. The principle active ingredients of the composition of the present invention are phytoene, which is a colorless carotenoid, and phytofluene, which has slight yellowish color. Thus, obtaining a light-color composition can be achieved by either selecting the additional carotenoid from carotenoids having a light color or by reducing the concentration of the colored carotenoid in the composition.

According to certain embodiments, the ratio of the concentration of the combined total amount of phytoene and phytofluene to the concentration of the additional carotenoid is from about 1:1 to about 50:1, alternatively from about 2:1 to about 25:1, still alternatively from about 4:1 to about 10:1.

According to certain embodiments, the additional carotenoid is zeta carotene. Zeta carotene is the first visible component in the biosynthesis pathway of colored carotenoids including beta-carotene and lycopene.

According to currently preferred embodiments, the composition has a yellow to light orange color. According to one embodiment, the composition has a light yellow color.

The carotenoid concentration in the composition can be measured by any method as is known to a person skilled in the art. Typically, carotenoid concentration is measured either by high-performance liquid chromatography (HPLC) methods or by spectrophotometer.

The conjugated double bond system constitutes the light-absorbing chromophore that gives carotenoids their color and provides their absorption spectrum that serves as a basis for their identification and quantification. Thus, the ultraviolet (UV) and visible spectrum is the first diagnostic tool for the identification and also quantification of carotenoids. The wavelength of maximum absorption ($\lambda$max) and the shape of the spectrum (spectral fine structure) are characteristic of the chromophore. The greater number of conjugated double bonds in a carotenoid the higher the maximum absorption values. Thus, the most unsaturated acyclic carotenoid lycopene, with 11 conjugated double bonds, has an intense red color, and it absorbs at the longest wavelength ($\lambda$max at 444, 470, and 502 nm, typically measured at an average of 450 nm). At least 7 conjugated double bonds are needed for a carotenoid to have a perceptible color; thus, zeta carotene is light yellow. Being also acyclic, its spectrum has three well-defined peaks, but theses are at wavelengths much lower than those of lycopene ($\lambda$max at 378, 400, and 425, typically measured at an average of 400 nm), commensurate with its 7 conjugated double bonds. Phytoene (with 3 conjugated double bonds) and phytofluene (5 conjugated double bonds) are colorless, with phytofluene sometime showing slight yellowish color. Phytoene absorbs maximally at 276, 286 and 297 (typically measured at an average of 286 nm) and phytofluene absorbs maximally at 331, 348, and 367 nm, typically measured at an average of 348 nm).

The absorption spectra of carotenoids are markedly solvent dependent, and the absorbance coefficient of a carotenoid (absorbance at given wavelength of a 1% solution in spectrophotometric cuvette with a 1-cm light path), which is used in the calculation of the concentration of a certain carotenoid varies significantly in different solvents. This has to be remembered in analyzing carotenoids in a certain composition, particularly when analysis is performed by HPLC in which different solvents may be used during the separation procedure.

The advantage of having a carotenoid composition which is devoid of intense color is that the carotenoids will not have strong effect on the aesthetic properties of the composition or on the skin color after administration, either when the composition is applied topically to the skin or when applied orally. In addition, the minor absorbance of light in the visible range renders the composition stable to degradation under visible light, and thus increases its bioavailability when applied topically to the skin as well as its shelf life.

Carotenoids for use in the compositions of the present invention can be obtained from any available source. They can be extracted from a natural source, can be synthesized chemically or can be obtained by methods of molecular genetics. Typically, they may be obtained from organisms that produce carotenoids, including a variety of plants, various algae, and certain microorganisms, including genetically modified organisms. Each of the carotenoids may be extracted from a different source, or phytoene, phytofluene and the additional carotenoid, potentially zeta-carotene, may be obtained from the same source.

According to certain embodiments, phytoene, phytofluene, zeta-carotene or any combination thereof is derived from a tomato fruit. Tomato fruit are typically characterized by the presence of high concentration of lycopene compared to the concentration of phytoene or phytofluene. According to certain embodiments, the process of carotenoids extraction from tomato fruit comprises a step of separating the desired carotenoids phytoene, phytofluene and zeta-carotene from any other carotenoids. According to other embodiments, the present invention utilized tomato varieties having low amount to non-detectable amount of carotenoids other than phytoene, phytofluene and zeta-carotene.

According to other embodiments, phytoene, phytofluene, zeta-carotene or any combination thereof is derived from an alga, preferably an alga of the species *Dunaliella*.

Carotenoid extraction from the organism or any of its parts can be performed by any method as is known to a person skilled in that art. According to certain embodiments, the organism or its part is immersed in a solvent, to extract oil soluble ingredients from the organism into the solvent. Extraction may be carried out after applying a pre-treatment. For example, when the source is a tomato fruit, the pre-treatment includes grinding and/or homogenizing the fruit. The extraction process may be accelerated by heating and/or stirring the source-solvent mixture. After removing non-extracted debris, the solvent may be removed. Examples of extract solvents include lower mono alcohols such as methyl alcohol, ethyl alcohol, 1-propanol, 2-propanol, 1-butanol and 2-butanol; lower alkyl esters such as ethyl acetate; hydrocarbons such as benzene, hexane and pentane; ketones such as acetone and methyl ethyl ketone; oils such as squalane, liquid paraffin, polydecene; ethers such as diethyl ether, tetrahydrofuran and dipropyl ether; and acetonitrile. One solvent as well as different solvent combinations may be used, as is known to a person skilled in the art. According to certain embodiments, the solvent is hexane, ethanol, ethyl acetate or any combination thereof.

The extract can be then further purified, for example by molecular weight fractionation, solvent fractionation, by purifying the oil soluble extract with any resin such as an ion-exchange resin or an absorbent resin, and the like. According to certain embodiments, the extraction solvent is removed, and the oil-soluble carotenoid preparation is mixed with a diluent suitable for cosmetics or for oral consumption. Such diluent can be a liquid to obtain a liquid formulation or a solid to obtain solid formulation. An example for phytoene and phytofluene extraction is described in U.S. Pat. No. 6,383,474 to some of the inventors of the present invention and co-workers, incorporated herein in its entirety by reference.

According to other embodiments, the carotenoids phytoene, phytofluene, zeta-carotene or any combination thereof are not extracted from the organism. Thus, according to certain embodiments, the carotenoid compositions of the present invention are in the form of powder, obtained by dehydration of the intact organism or a part thereof. Organisms or parts thereof that can be dehydrated to provide the compositions of the present invention include, for example, tomato fruit, algae and fungi.

In addition to obtaining phytoene, phytofluene and zeta-carotene from a natural source, these carotenoids can also be synthesized by any of the known chemical or biochemical methods or by recovering these carotenoids from a genetically modified source. Chemically, phytoene can be synthesized, for example, from two geranylgeranyl pyrophosphates (C-20), in a reaction which may be mediated by phytoene synthase. The geranylgeranyl pyrophosphate can be obtained directly, by the conversion of mevalonic acid or by the condensation of pyruvate and glyceraldehyde-3-phosphate. Phytofluene can be synthesized by desaturation of phytoene, a reaction which may be mediated by phytoene desaturase. Further desaturation steps lead to the production of zeta-carotene. A genetically modified source can be obtained, for example, by the mutagenesis of enzymes which are active downstream to phytofluene in a carotenoid-producing organism. Such synthesized phytoene, phytofluene and zeta-carotene will have activities that are substantively similar to the activities of these carotenoids obtained from organisms that produce carotenoids as described hereinabove.

Modes of Administration

The combination of phytoene and phytofluene can exert its whitening effect, among other cosmetic effects on skin either when topically applied to the skin or when consumed orally. It is to be understood that the amount of the carotenoids within the composition depends on the rout of administration, the phenomenon to be treated and on parameters related to the user including age, gender and application regime.

Topical Application

For topical application, the oil-soluble carotenoid preparation obtained by any of the methods described hereinabove is mixed with a cosmetically acceptable diluent selected from the group consisting of, but not limited to, squalane, squalene, liquid paraffin, jojoba oil, sunflower oil and polydecene. The cosmetic composition such prepared is highly tolerated by skin, and thus suitable for topical application to reach the cosmetic effects, including promotion of skin whitening, lightening of skin color, evening or harmonization of skin tone and/or color, reduction of pigmentation, reduction of pigmentation after UV exposure, reduction in the appearance of solar lentigines (age spots) or ephilides (freckles), reduction of melasma, reduction of chloasma, reduction of post-inflammatory hyperpigmentation reduction of pigmented keratoses and the like. According to certain embodiments the diluent is squalane, typically squalane derived from a natural source. Typical sources for natural squalane include olive oil, wheat germ and sesame.

The cosmetic compositions for use according to the method of the present invention can be formulated for topical use in a form selected from the group consisting of, but not limited to, cream, ointment, lotion, gel, foam, suspension, aqueous or cosolvent solutions, salve, liposomes and any other cosmetically acceptable form suitable for topical administration of the carotenoid preparation. The composition may also form part of a patch for transdermal application.

Thus, according to certain embodiments, the compositions of the present invention further comprise diluent, excipient or carrier.

In some embodiments the topical formulation is selected from the group consisting of emulsions, non-washable (water-in-oil) creams or washable (oil-in-water) creams, lotions, salves and the like.

As is well known in the art the physico-chemical characteristics of the diluent may be manipulated by addition of a variety of excipients, including but not limited to thickeners, gelling agents, wetting agents, flocculating agents, suspending agents and the like. These optional excipients will determine the physical characteristics of the resultant formulations such that the application may be more pleasant or convenient. It will be recognized by the skilled artisan that the excipients selected, should preferably enhance and in any case must not interfere with the activity of the active ingredient and with the storage stability of the formulations.

The concentration of the oil-soluble carotenoid containing fraction in the topical compositions is in the range of 0.0001-50% (w/w) and preferably in the range of 0.01-10% (w/w).

Oral Administration

It has been previously shown that dietary carotenoids are present in the skin. Hata et al., (J. Invest. Dermatology 115: 441-448, 2000) showed that among others, phytoene, phytofluene and zeta-carotene are present in human abdominal skin extract in significant quantities. It has been also shown that carotenoids useful as photoprotectants when applied topically are also effective when the carotenoids are provided with the diet (Tronnier and Heinrich, Int. J. Vitam. Nutr. Res. 75(1):54-60, 2005).

Thus, according to certain embodiments, the compositions of the invention are formulated for oral administration in a form selected from liquid and solid dosage forms.

In some embodiments the compositions for oral administration are formulated in a form selected from the group consisting of solutions, suspensions, dry soluble lyophilized powders, emulsions, microemulsions, dispersions, liposomal dosage forms, lipid complexes such as with cholesterol derivatives and phospholipids, capsules, soft gel capsules and the like.

In other embodiments the solutions and vehicles are selected from aqueous and non-aqueous solutions. Optionally, at least one additional ingredient selected from the group consisting of preservatives, antioxidants and tonicity controlling agents may be added to the formulation. In one embodiment the preservatives are selected from the group consisting of benzyl alcohol, methyl paraben, propyl paraben, and sodium salts of methyl paraben.

In another embodiment the tonicity controlling agents are selected from the group comprising of sodium chloride, mannitol, dextrose, glucose, lactose and sucrose.

In other embodiments the compositions of the present invention are solid compositions for oral administration selected from the group consisting of tablets, capsules, sachets, powders, granules and lozenges.

In certain embodiments the solid pharmaceutical composition formulated as tablets contain in addition to the active compound suitable excipients including, but not limited to, starches, gum arabic, calcium silicate, microcrystalline cellulose, polyvinylpyrrolidone, cellulose, water, syrup, and methylcellulose. The formulations can additionally include lubricating agents such as, for example, talc, magnesium stearate and mineral oil; wetting agents; emulsifying and suspending agents; preserving agents such as methyl- and propyl hydroxybenzoates; sweetening agents; or flavoring agents. Polyols, buffers, and inert fillers may also be used. Examples of polyols include, but are not limited to: mannitol, sorbitol, xylitol, sucrose, maltose, glucose, lactose, dextrose, and the like. Suitable buffers encompass, but are not limited to, phosphate, citrate, tartarate, succinate, and the like. Other inert fillers, which may be used, encompass those which are known in the art and are useful in the manufacture of various dosage forms. If desired, the solid compositions may include other components such as bulking agents and/or granulating agents, and the like. The compositions can be formulated so as to provide quick, sustained, or delayed release of the carotenoids after administration to the subject by employing procedures well known in the art.

The concentration of the oil-soluble carotenoid containing fraction in an oral dosage form is in the range of 0.0001-50% (w/w) and preferably in the range of 0.1-10% (w/w).

The following examples are presented in order to more fully illustrate the preferred embodiments of the invention. They should in no way be construed, however, as limiting the broad scope of the invention.

EXAMPLES

Example 1

Effect of Tomato-Derived Carotenoid Extract (IBR-TCLC®) on Melanin Synthesis in Cultures of Normal Human Melanocytes and Murine B16 Melanoma Cells Materials and Methods
Cells and Culture Conditions

| | |
|---|---|
| Cell type: | Normal human epidermal melanocytes (NHEM-2) used at 6th passage. |
| Culture medium: | Medium 254 (Basal Medium for Human Melanocytes, Tebu-bio France, 058M-254-500) + complement HMGS-2 without PMA (Tebu-bio France, 058S-016-5) |
| | Penicillin 50 UI/ml and streptomycin 50 µg/ml (Invitrogen 15070063) |
| Cell type: | B16 murine melanoma cell line (B16), used at 5th passage. |
| Culture medium: | DMEM (Invitrogen 21969035) |
| | L-glutamine 2 mM (Invitrogen 25030024) |
| | Penicilline/streptomycine 50 UI/ml/50 µg/ml (Invitrogen 15070063) |
| | Fetal calf serum 10% (v/v, Invitrogen 10270098) |
| Culture: | 37° C. and 5% CO2 |

Test Compound and References

| | Stock Solution | Dilution | Final Tested Concentrations |
|---|---|---|---|
| Test Compound | | | |
| IBR-TCLC ® (tomato colorless carotenoids) in DMSO; Batch TCD-5013/1 (AD050613/1) Phytoene and Phytofluene (P&P): 1.5 mg/ml Other carotenoids: Non-detectable | IBR-TCLC ® in DMSO stored at 4° C. | Medium supplemented with 0.5% DMSO | 0.5% (7.5 µg/ml) (0.5% DMSO final) |

| | Stock Solution | Dilution | Final Tested Concentrations |
|---|---|---|---|
| Dimethylsulfoxide (DMSO, AD050613/2) Reference | Solvent used in this study | | 0.5% final |
| Isobutylmethyl xanthine (IBMX, Sigma I7018) | 500 mM in culture medium | In culture medium | 200 μM |
| Kojic Acid (KA, Sigma K3125) | 10 mg/ml (1%) in culture medium | In culture medium | 0.04%, 0.0036% and 0.00156% |

Culture Conditions
Normal Human Epidermal Melanocytes

The R6-NHEM-2 cells were cultivated in 24 well plates (120,000 cells/well). At 50% confluence, culture media were replaced by fresh media containing or not containing (control) the test compound, KA or IBMX (references) or DMSO at a final concentration of 0.5% (control DMSO). Each experimental condition was examined in triplicate (hexaplicate for control). The cells were incubated at 37° C. for 240 hours with medium change every 3 days.

B16 Murine Melanoma Cell Line

The R7-B16 cells were cultivated in 24 well plates (1000 cells/well). At 20% confluence, culture media were replaced by fresh media containing or not containing (control) the test compound, KA or IBMX (references) or DMSO at a final concentration of 0.5% (control DMSO). Each experimental condition was examined in triplicate. The cells were incubated at 37° C. for 144 hours with medium change after 3 days (2×72 h).

Melanin Assay

After incubation, the cell monolayers were rinsed, the cells were lysed and melanin was extracted by a solution 0.5 M NaOH. The optical density (OD) of each experimental point was measured at 405 nm against melanin standards (standard curve 0.39 to 100 μg melanin/ml solution, Sigma M8631). Results were expressed in μg melanin/ml and in percent of the negative control.

Data Management

The raw data were transferred to and analyzed with PRISM® software (Graph Pad Software). The inter-group comparisons were performed by variance analysis (ANOVA) with multiple comparison test of Dunnett.

Results and Conclusion
Effect of IBR-TCLC® on Melanin Content of B16 Murine Melanoma Cell Line Table 1 hereinbelow and FIG. 1 show the effect of IBR-TCLC® and reference compounds on melanin synthesis by B16 murine melanoma cells (B16).

The reference compound "kojic acid" tested at 0.04% slightly decreased the melanin content of B16 murine melanoma cells (88% of control). The reference "IBMX" tested at 200 μM, strongly increased the melanin content (731% of control, p<0.01). These values were expected in this type of assay.

The presence of DMSO at a final concentration of 0.5% in the culture medium strongly increased the melanin content of B16 melanocytes (3 fold stimulating factor).

In these experimental conditions, the compound IBR-TCLC® tested at 0.5% (0.5% DMSO final) decreased the melanin content of B16 murine melanoma (22% inhibition compared to the control DMSO). In these experimental conditions, no cytostatic effect was observed on B16 murine melanocytes in cultures (data not shown).

TABLE 1

Melanin Assay - B16 Murine Melanoma

| Treatment | Conc. | Melanin (μg/ml) | sd | n | % of control | p |
|---|---|---|---|---|---|---|
| Control | — | 17.0 | 0.6 | 3 | 100 | — |
| Kojic Acid | 0.04% | 14.9 | 1.2 | 3 | 88 | p > 0.05 |
| IBMX | 200 μM | 124.2 | 5.0 | 3 | 731 | p < 0.01 |
| Control DMSO | 0.5% | 48.3 | 4.6 | 3 | 100 | — |
| IBR-TCLC ® (0.5% DMSO) | 0.5% | 37.5 | 0.1 | 3 | 78 | p < 0.01 |

Figure 2:
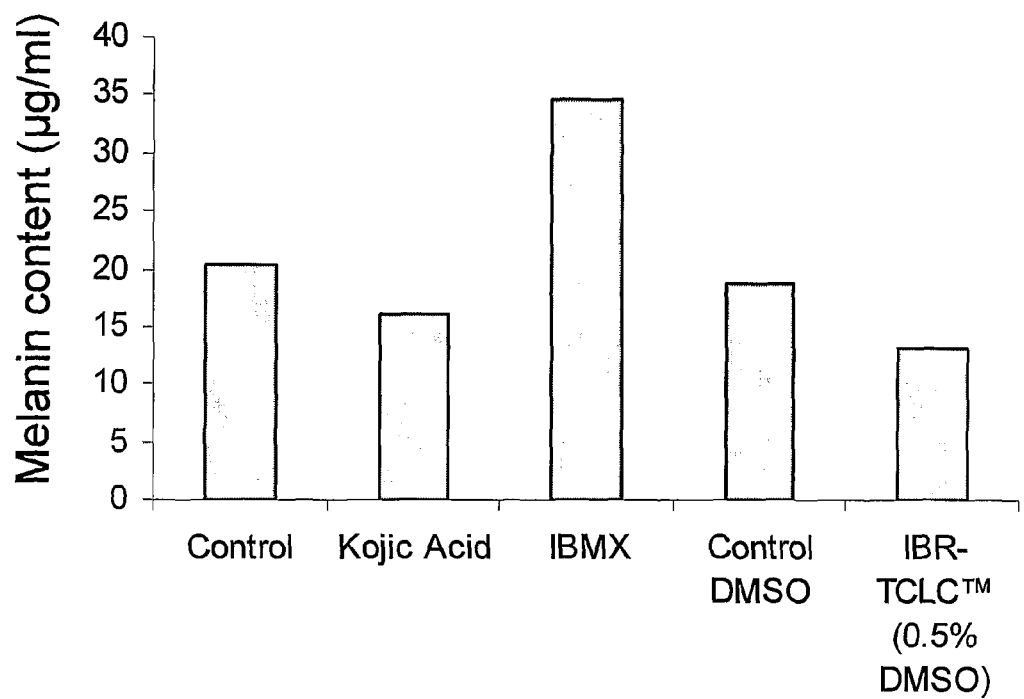
FIG. 2 shows the effect of the compound IBR-TCLC® and reference compounds on melanin synthesis by normal human melanocytes (NHEM).

Effects of IBR-TCLC® on Melanin Content of Normal Human Epidermal Melanocyte Culture Table 2 herein below and FIG. 2 show the effect of IBR-TCLC® and reference compounds on melanin synthesis by human epidermal melanocyte cells.

The reference compound "kojic acid" tested at 0.0036% and 0.00156% induced a significant dose-dependent decrease of the melanin content (respectively 67% and 79% of control, p<0.01). The reference "IBMX" tested at 200 μM, significantly increased the melanin content (171% of control, p<0.01). These values were expected in this type of assay and validated the assay.

In these experimental conditions, the compound "IBR-TCLC®" tested at 0.5% significantly decreased the melanin content of normal human melanocytes (71% compared to the control DMSO).

TABLE 2

Melanin Assay - Normal Human Melanocytes

| Treatment | Conc. | Melanin (μg/ml) | sd | n | % of control | P |
|---|---|---|---|---|---|---|
| Control | — | 20.3 | 1.3 | 6 | 100 | — |
| Kojic Acid | 0.0036% | 13.6 | 1.2 | 3 | 67 | p < 0.01 |
| | 0.00156% | 16.1 | 1.6 | 3 | 79 | p < 0.01 |
| IBMX | 200 μM | 34.7 | 0.8 | 3 | 171 | p < 0.01 |
| Control DMSO | 0.5% | 18.7 | 1.5 | 3 | 100 | — |
| IBR-TCLC ® (0.5% DMSO) | 0.5% | 13.2 | 0.4 | 3 | 71 | p < 0.01 |

Example 2

Effect of IBR-TCLC® in Squalane on Melanin Formation and Whitening

Tomato-derived composition of phytoene and phytofluene was dissolved in Squalane from olive oil (Phytoene and Phytofluene combined total concentration: 0.724 mg/ml). Other carotenoids were non-detectable in this composition. This composition was used at final concentrations of 0.3%, 0.5% and 1.0% to assess its whitening effect on B16 murine melanoma cells.

B16 murine melanoma cells were cultured in MEM medium at 37° C., 5% $CO_2$. Next day, the cells were treated with 0, 0.25%, 0.5% 1.25%, 3.75% and 5% of the squalane tomato extract. By "treated" it is meant that the incubation medium was replaced and the squalane tomato extract was added to reach a final concentration as described above. After 4 days the cells were collected by centrifugation. Whitening effect was evaluated by evaluating the color of the cell pellets with as follows:

(++): Extremely white compared to the pellet of cell that received no treatment (control); (+): Obviously white compared to control; (−): No effect The viability of all treated cells was measured as follows: Cells were transferred to another plate, fixed with formalin and dyed by adding 1% crystal violet solution. The cell viability was measured with MONOCELLATER (Olympus Optical Company), essentially according to the manufacturer instructions. No toxicity effect on B16 melanoma cultured cell was observed (see table 3 below).

TABLE 3

Whitening Effect of Squalane Tomato Extract on Melanoma Cells

| | Concentration (%) | | | | | |
|---|---|---|---|---|---|---|
| | 0 | 0.25 | 0.5 | 1.25 | 3.75 | 5.0 |
| Whitening effect | − | − | + | ++ | ++ | ++ |
| Cell viability (%) | 100 | 106 | 112 | 104 | 101 | 98 |

The results shown in Example 1 and Example 2 above demonstrate that a composition comprising the carotenoids phytoene and phytofluene, having non-detectable amounts of other carotenoids, is highly effective in inhibiting melanin content in normal as well as cancerous skin cells. Moreover, such composition, which is essentially devoid of colored carotenoids like beta-carotene and lycopene, is very stable. In addition, being uncolored, the phytoene-phytofluene composition is highly suitable for cosmetic use as it does not contribute any coloration to the cosmetic preparation.

Example 3

Preparation of Facial Cleanser

A. Ingredients (1) to (7) described below are mixed and dissolved under heating to obtain mixture A.
B. Ingredients (8) to (11) described below are mixed and dissolved under heating to obtain mixture B.
C. Mixture B is added to mixture A to obtain mixture C.
D. Mixture C is cooled, and then ingredients (12) to (14) described below are added and mixed to give a facial cleanser.

| Ingredient | mass % |
|---|---|
| (1) Lauric acid | 5.0 |
| (2) Myristic acid | 18.5 |
| (3) Stearic acid | 6.0 |
| (4) Glycerin | 12.0 |
| (5) Polyethylene glycol 1500 | 5.0 |

| Ingredient | mass % |
|---|---|
| (6) Potassium hydroxide | 6.5 |
| (7) Purified water | balance |
| (8) Coconut oil fatty acid diethanol amide | 5.0 |
| (9) Coconut oil fatty acid methyl taurine sodium | 1.8 |
| (10) Polyoxy ethylene (7.5 E.O.) lauryl ether | 2.0 |
| (11) Ethylene glycol distearate | 1.0 |
| (12) One % aqueous solution of hydroxyl propylmethyl cellulose | 5.0 |
| (13) Squalane tomato extract * | 0.1 |
| (14) Fragrance | q.s. |

* Produced as in Example 1A
q.s. sufficient quantity

Example 4

Preparation of Skin Lotion

A. Ingredients (1) to (6) described below are mixed and dissolved to obtain mixture A.
B. Ingredients (7) to (12) described below are mixed and dissolved to obtain mixture B.
C. Mixture B is added to Mixture A to give a skin lotion.

| Ingredient | mass % |
|---|---|
| (1) Citric acid | 0.05 |
| (2) Sodium citrate | 0.2 |
| (3) Sodium pyrrolidone carboxylate (50%) solution | 0.5 |
| (4) Dipotassium glycyrrhizinate | 0.1 |
| (5) Glycerin | 3.5 |
| (6) 1,3-butylene glycol | 8.0 |
| (7) Purified water | balance |
| (8) Ethanol | 10.0 |
| (9) Squalane tomato extract * | 0.05 |
| (10) Fragrance | q.s. |
| (11) Preservative | q.s. |
| (12) Mono oleic polyoxy ethylene (20 E.O.) sorbitan | 0.5 |

* Produced as in Example 1A
q.s. sufficient quantity

Example 5

Preparation of Milky Lotion

A. Ingredients (1) to (13) described below are mixed, dissolved under heating and kept to 70° C. to obtain mixture A.
B. Ingredients (14) to (18) described below are mixed, dissolved under heating and kept to 70° C. to obtain mixture B.
C. Mixture B is added to the mixture A to be emulsified, and ingredient (19) is added, to obtain mixture C.
D. Ingredient (20) is added to mixture C to give a milky lotion.

| Ingredient | mass % |
|---|---|
| (1) Stearic acid | 1.0 |
| (2) cetyl alcohol | 0.5 |
| (3) Hydrophilic type mono stearic glycerin | 0.5 |
| (4) Liquid paraffin | 2.0 |
| (5) Squalane | 2.9 |
| (6) Jojoba oil | 3.0 |
| (7) Cetyl palmitate | 0.2 |
| (8) Retinol palmitate | 0.2 |

-continued

| Ingredient | mass % |
| --- | --- |
| (9) Tocopherol acetate | 0.05 |
| (10) Squalane tomato extract * | 0.2 |
| (11) Preservative | q.s. |
| (12) Sorbitan monostearate | 0.3 |
| (13) Mono oleic polyoxyethylene (20 E.O.)sorbitan | 0.5 |
| (14) Triethanol amine | 0.5 |
| (15) 1,3-butylene glycol | 15.0 |
| (16) Glycerin | 3.0 |
| (17) Polyethylene glycol 6000 | 0.5 |
| (18) Purified water | balance |
| (19) One % solution of carboxy vinyl polymer | 8.0 |
| (20) Fragrance | q.s. |

* Produced as in Example 1A

Example 6

Preparation of Skin Cream

A. Ingredients (1) to (14) described below are mixed, dissolved under heating and kept at 70° C. to obtain mixture A.

B. Ingredients (15) to (19) described below are mixed under heating and kept at 70° C. to obtain mixture B.

C. Mixture B is added to Mixture A to be emulsified, and ingredient (20) is added to obtain mixture C.

D. Mixture C is cooled; ingredient (21) is added and mixed to give a skin cream.

| Ingredient | mass % |
| --- | --- |
| (1) Stearic acid | 2.5 |
| (2) Cetyl alcohol | 2.5 |
| (3) Hydrophilic type mono stearic glycerin | 2.0 |
| (4) Vaseline | 2.0 |
| (5) Dipenta erythritol fatty acid ester* | 2.0 |
| (6) Isotridecyl myristate | 5.0 |
| (7) Liquid paraffin | 8.0 |
| (8) Squalane | 4.95 |
| (9) Yellow beeswax | 1.0 |
| (10) Squalane tomato extract** | 0.15 |
| (11) Cetyl palmitate | 2.0 |
| (12) Sorbitan sesqui oleate | 0.5 |
| (13) Mono oleic polyoxyethylene (20 E.O.) sorbitan | 1.5 |
| (14) Preservative | q.s. |
| (15) Triethanol amine | 1.2 |
| (16) 1,3-butylen glycol | 8.0 |
| (17) Glycerin | 2.0 |
| (18) Polyethylene Glycol 20000 | 0.5 |
| (19) Purified water | balance |
| (20) One % aqueous solution of carboxy vinyl polymer | 10.0 |
| (21) Fragrance | q.s. |

*"COSMOL 168AR" produced by Nisshin OilliO, Ltd.
**Produced as in Example 1A

All of the cosmetic compositions obtained as described in Examples 4-6 hereinabove are uncolored, homogenous without showing any separation, and therefore having excellent stability.

All these compositions could make the skin beautiful, white and clear when being applied to the skin at least once a week up to twice per day.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method of whitening skin of a subject having undesired skin pigmentation by reducing melanin content within the skin cells of the subject in need thereof, the method comprising administering to the subject having undesired skin pigmentation a composition comprising a combination of phytoene and phytofluene, the combination of phytoene and phytofluene being in an amount sufficient to reduce the melanin content in the skin cells of the subject, thereby whitening the undesired skin pigmentation of the subject by reducing the melanin content within the skin cells of the subject wherein the undesired skin pigmentation is not caused by UV exposure.

2. The method according to claim 1, wherein the composition is essentially colorless.

3. The method according to claim 1, wherein the composition further comprises at least one additional carotenoid other than phytoene and phytofluene.

4. The method according to claim 3, wherein the at least one additional carotenoid is selected from the group consisting of zeta-carotene, beta-carotene, lycopene, zeaxanthin, astaxanthin, cataxanthin, zeaxanthin, lutein, canthaxanthin and any combination thereof.

5. The method according to claim 4, wherein the at least one additional carotenoid is zeta-carotene.

6. The method according to claim 3, wherein the ratio of the concentration of the combined total amount of phytoene and phytofluene to the concentration of the at least one additional carotenoid is from about 1:1 to about 50:1.

7. The method according to claim 3, wherein the composition is devoid of intense color.

8. The method according to claim 3, wherein the phytoene, the phytofluene, and the at least one additional carotenoid or combinations thereof is derived from a plant or a plant part.

9. The method according to claim 8, wherein the plant is tomato plant and the plant part is tomato fruit.

10. The method of claim 3, wherein the phytofluene the at least one additional carotenoid or combinations thereof is derived from an algae of the species *Dunaliella*.

11. The method according to claim 3, wherein the phytoene, phytofluene and at least one additional carotenoid are obtained by chemical synthesis.

12. The method according to claim 3, wherein the phytoene, phytofluene and at least one additional carotenoid are recovered from a genetically modified source.

13. The method according to claim 1, wherein the composition further comprises at least one active ingredient selected from the group consisting of an anti-oxidant, an anti-inflammatory agent, a moisturizer, a vitamin, a UV absorbing agent, a UV protecting agent, skin whitening agent or any combination thereof.

14. The method according to claim 1, wherein the composition is administered in a form selected from topical administration to the skin, oral administration and a combination thereof.

15. The method of claim 3, wherein the phytoene, the phytofluene, and the at least one additional carotenoid or combinations thereof are derived from a natural source selected from the group consisting of a fungi and a microorganism.

* * * * *